United States Patent [19]

Horvath

[11] 4,377,305
[45] Mar. 22, 1983

[54] ARTIFICIAL HAND

[75] Inventor: Eduard Horvath, Vienna, Austria

[73] Assignee: Otto Bock Orthopädische Industrie KG, Duderstadt, Fed. Rep. of Germany

[21] Appl. No.: 226,613

[22] PCT Filed: May 20, 1980

[86] PCT No.: PCT/AT80/00015
§ 371 Date: Jan. 21, 1981
§ 102(e) Date: Jan. 21, 1981

[87] PCT Pub. No.: WO80/02500
PCT Pub. Date: Nov. 27, 1980

[30] Foreign Application Priority Data

May 21, 1979 [AT] Austria ............................ 3735/79

[51] Int. Cl.³ .......................... A61F 1/06; B25J 15/00
[52] U.S. Cl. ...................................... 294/106; 3/12.7; 3/12.8
[58] Field of Search .................. 294/86 R, 88, 106; 3/12, 12.4, 12.6-12.8; 414/732, 735, 739, 744 A, 753

[56] References Cited

U.S. PATENT DOCUMENTS

| | | | |
|---|---|---|---|
| 2,449,728 | 9/1948 | Snethun | 3/12.6 |
| 2,668,959 | 2/1954 | Sargeson | 3/12.6 |
| 3,227,290 | 1/1966 | Lemelson | 414/739 X |
| 3,247,978 | 4/1966 | Neumeier | 414/735 |
| 3,263,535 | 8/1966 | Zurcher | 294/106 X |
| 3,312,496 | 4/1967 | Boutelle et al. | 294/88 X |
| 3,362,545 | 1/1968 | Rowe | 294/106 X |
| 3,509,583 | 5/1970 | Fraioli | 414/5 X |
| 3,572,807 | 3/1971 | Haaker et al. | 294/106 |
| 3,692,161 | 9/1972 | Katsuren et al. | 188/134 X |
| 3,927,424 | 12/1975 | Itoh | 294/106 X |
| 3,952,880 | 4/1976 | Hill et al. | 294/106 X |
| 4,149,278 | 4/1979 | Frosch et al. | 3/12.5 |

FOREIGN PATENT DOCUMENTS

| | | | |
|---|---|---|---|
| 697518 | 11/1964 | Canada | 294/106 |
| 1296752 | 5/1962 | France | 3/12.8 |

Primary Examiner—Johnny D. Cherry
Attorney, Agent, or Firm—Karl F. Ross; Herbert Dubno

[57] ABSTRACT

This hand is provided with two clamping jaws (1,2) movable toward or respectively apart from each other, each of which is mounted in each case to a hinge quadrangle (3, 4). At each clamping jaw (1, 2) there is supported a gripping plate (8, 9) tiltable around an axis (5, 6) vertical to the jaw axis. The two hinge quadrangles (3, 4) can be rotatably supported jointly by an axis running parallel to the hinge axes of the hinge quadrangles (3, 4), however, also the two hinge quadrangles can be jointly tiltable around one axis, which runs vertical to the hinge axes (FIG. 3).

8 Claims, 6 Drawing Figures

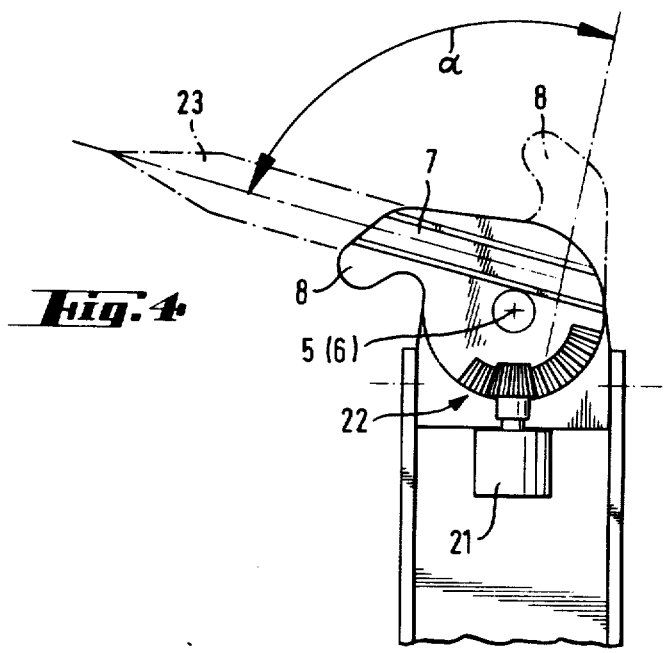
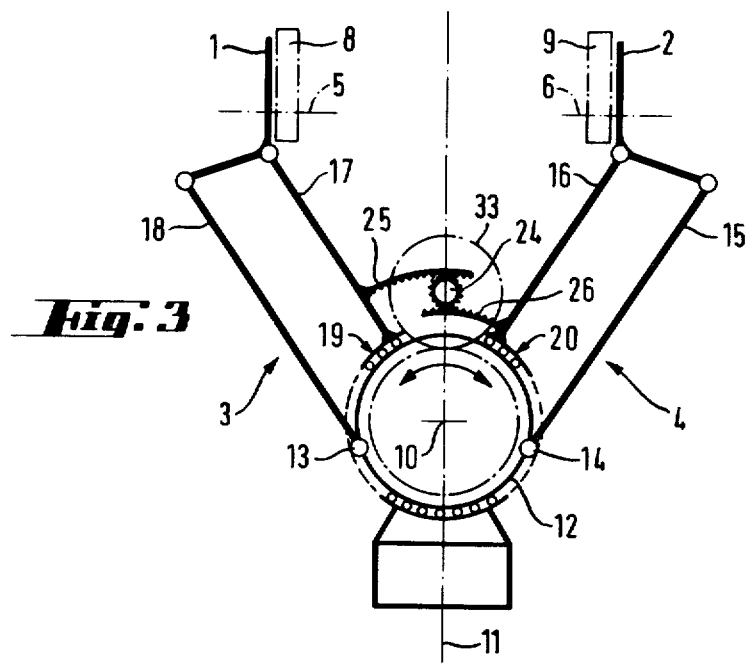

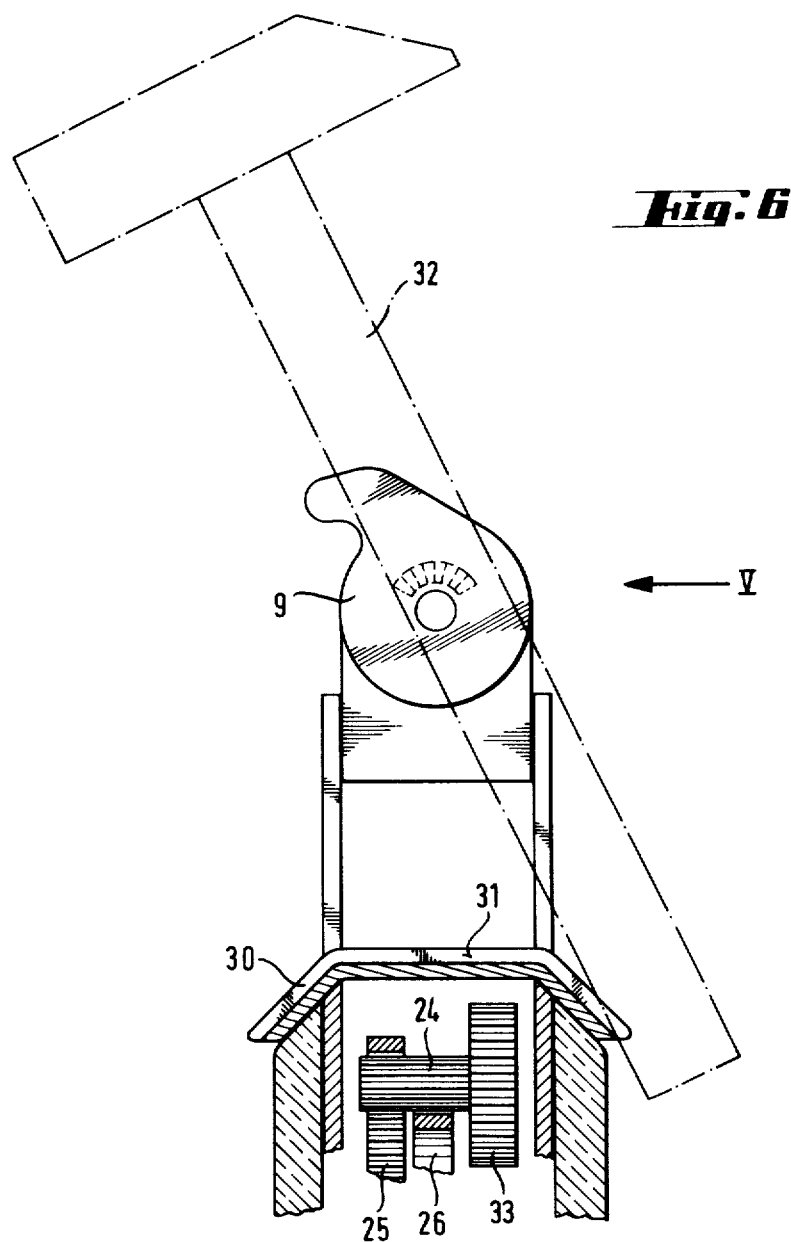

ARTIFICIAL HAND

CROSS REFERENCE TO RELATED APPLICATION

This application is a national phase application of PCT application PCT/AT80/00015 filed May 25, 1980 and based upon Austrian application Ser. No. A 3735/79 filed May 21, 1979 under The International Convention.

FIELD OF THE INVENTION

The invention relates to an artificial hand, which is provided with two clamping jaws or the like movable towards each other and away from each other for gripping of objects. Each clamping jaw is mounted to a hinge quadrangle and more particular to a hingeparallelogram.

OBJECT OF THE INVENTION

It is an object of the invention to form such a hand so that the object gripped (after the gripping) can be brought into as many different positions as possible.

SUMMARY OF THE INVENTION

This object is achieved with an artificial hand having a gripping plate, preferably provided with a groove, at each clamping jaw, the gripping plate being tiltable around an axis perpendicular to the plane of the jaw. The two hinge quadrangles can be tilted jointly around an axis which is parallel to the hinge axes of the hinge quadrangles or the two hinge quadrangles can be jointly tiltable by preferably 180° around an axis directed perpendicularly to the hinge axis. The tiltable disposition of the gripper plate at the clamping jaws allows the gripped object to be brought into arbitrary positions within the tilting range in a plane parallel to the clamping jaws. If in addition the two hinge quadrangles jointly are tiltable around a joint axis directed parallel to the hinge axes of the hinge quadrangles, then the plane of the gripper plates is itself tiltable. In addition or instead of providing tiltability of the two hinge quadrangles around the axis directed parallel to the hinge axes, the two hinge quadrangles can also be jointly tiltable around an axis directed perpendicular to the hinge axes and it allows for movability to place a gripped object in additional spacial positions.

A constructive simplification of the construction of the gripping hand and additional advantageous relations for the control of the high clamping forces by only small parts is achieved, if the axis parallel to the hinge axes, around which axis the two hinge parallelograms are jointly tiltable, is also an ideal hinge axis belonging to both jointly. A ring can be disposed concentrically to this axis which carries an additional hinge axis of the hinge parallelograms and the parallelogram are guided rotatably on the ring, for example by circular bearings disposed concentrically to the ring.

In order to achieve a simply constructed drive for the clamping of an object there can be provided as an additional feature of the invention a pinion at the drive for the tilting together or apart of the of the two hinge quadrangles. The pinion can engage at the same time two toothed segments, one of which is attached to the guide of each hinge quadrangle.

A preferred further feature comprises in this case that a motor with a drive is provided along the axis, which drives via a gearwheel the pinion along the axis and in particular that the drive disposed along the axis is switchable such that as desired the pinion or the ring can be driven.

In another embodiment of the invention there is provided for a pure manual operation a manual drive such as a handwheel for tilting of the two clamping plates or for the joint rotation of the hinge quadrangles around the axis.

It is an advantage for the practical handling, if in a practical embodiment of the invention one of the gripper plates is drivable by a motor and preferably by a bevel gear drive, whereas the other gripper plate is displaced by an object clamped between the two gripper plates, for example engaging in grooves of the two gripper plates.

In a further embodiment of the invention in the free space between the clamping jaws or the hinge quadrangles carrying them there is provided an exchangeable bridge covering the drive parts, which bridge preferably is provided at its upper side with groove-like guide surfaces.

BRIEF DESCRIPTION OF THE DRAWINGS

Additional features, details and advantages of the invention result in the following from the description by way of two embodiments shown in the drawing; in the drawing:

FIG. 3 is a schematic illustration of the kinematics of the hand in accordance with the present invention;

FIG. 4 is a detail of the region A shown in FIG. 2 in an enlarged scale; and

FIG. 5 is a side view and FIG. 6 is a section along line VI—VI of another embodiment.

SPECIFIC DESCRIPTION

Figure 1:
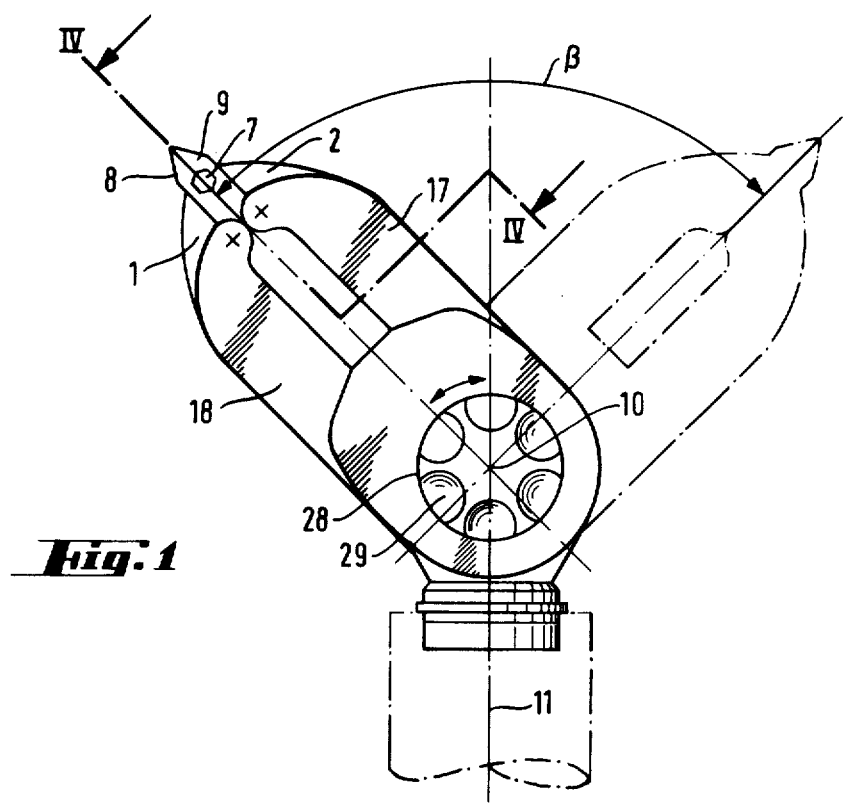
FIG. 1 is a schematic plan view of an artificial hand in accordance with the invention.

The artificial hand in accordance with the present invention is provided with two clamping jaws 1,2 movable toward each other and away from each other.

The kinematics of the drive for the motion of these clamping jaws 1 and 2 is herein effected by hinge quadrangles 3,4 (see FIG. 3), which are formed such as to assure that the two clamping jaws 1 and 2 in each position are maintained substantially parallel to each other. In particular the hinge quadrangles 3 and 4 are formed substantially as hinge parallelograms as can be seen from FIG. 3.

Each clamping jaw 1 and 2 is provided with a gripper plate 8,9 tiltable around an axis 5,6 perpendicular to the jaw plane. In order to allow for good support for rod shaped articles 23 such as lead pencils and the like by the gripper plates 8 and 9, these gripper plates are provided with mutually confronting grooves 7.

Both hinge quadrangles 3 and 4 are jointly swingable around an axis 10, which runs parallel to the hinge axes of the hinge quadrangles 3, 4.

In addition the two hinge quadrangles 3, 4 are jointly movable around an axis 11, which runs perpendicular to the axes of the hinge quadrangles 3, 4.

Figure 2:
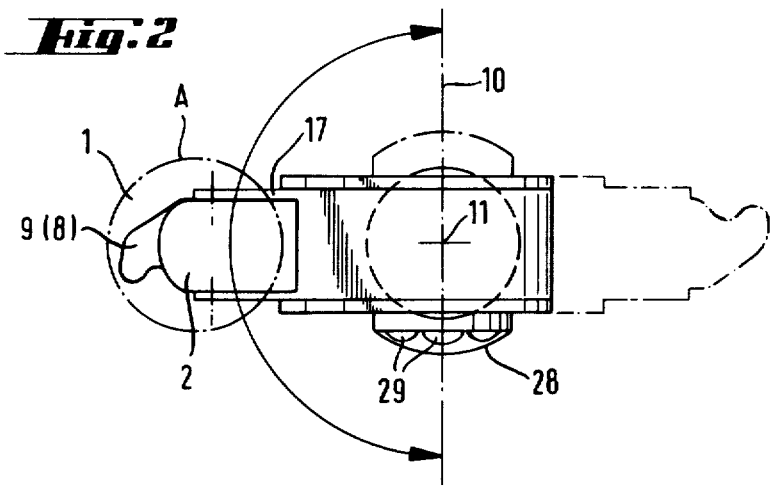
FIG. 2 is a horizontal projection corresponding to FIG. 1.

As can be recognized from FIG. 2, the hinge quadrangles 3,4 can be tilted around an axis 11 through an angle of 180°. The gripper plates 8 and 9 can be provided with hook-like extensions to allow the gripping hand to engage loops, eyelets and the like, which are displaced on the objects to be manipulated.

The axis 10, around which the two hinge quadrangles are jointly tiltable, is also one hinge axis jointly belonging to the two, that is extensions of the limbs 16, 17 run through this axis 10 (FIG. 3). A ring 12 concentrically disposed to the axis 10 is provided for receiving the hinge axes of the hinge quadrangles. The parallelogram limbs 16, 17, which run substantially parallel to the parallelogram limbs 15, 18 tiltably disposed relative to the ring 12, are tiltably guided on the ring 12. For the guiding herein the limbs 16, 17 are provided with (in part shown in dashed lines) ring bearings 19, 20, which are supported by rollers or like bodies next to each other.

As is shown in FIG. 4, one gripper plate 9 can be driven by a motor 21 via a bevel gear drive 22. The other gripper plate P is entrained by the clamped object 23 between the gripper plates 8,9. The two tilt axes 10 and 11, around which the hinge quadrangles 3 and 4 can be jointly tilted, preferably intersect each other. Each (not shown) drive, with which the two hinge quadrangles 3, 4 can be tilted toward and away from each other around the axis 10, is provided with a motor with drive and pinion 24, which at the same time engages two toothed segments 25, 26, of which one in each case is attached to the limb 16 and 17, respectively. Advantageously, this drive is switchable in the axis 10 for driving either the ring 12 or via a gearwheel 33 the pinion 24. Particularly advantageous is here the provision of a spin-resistant drive.

In FIG. 4 the angle is designated as α with which the gripper plates 8, 9 are tiltable around the axis 5 or respectively 6 disposed vertical to the clamping jaws 1 or respectively 2. This angle is preferably 90°. The axis 10 running parallel to the hinge axes allows a tilting by an angle β of the magnitude of again about 90°. The two hinge quadrangles 3, 4 can also be tilted around the axis 10.

The gripper plates 8, 9 can be dismountably connected, that is replaceably connected, with the clamping jaws 1, 2. In order to be able to employ for special manipulations differently formed gripper plates 8, 9, these are attached to the clamping jaws 1, 2 by way of a simply disconnectable connection, such as for example by a catch device.

In addition, a handwheel 28 is provided for tilting of the two clamping jaws 1, 2 or respectively for the joint tilting of the hinge quadrangles 3,4 around an axis 10. The handwheel 28 is provided with gripping recesses 29. This handwheel 28 is rotatably supported around the axis 10 and is coupled solidly or for each case with the drive for the hinge quadrangles; this way it allows a manual drive or respectively a manual amplification of the gripping force built up by this drive.

The gearwheel drive 22 can also be replaced by a catch provision, by the aid of which the gripper plates 8, 9 are fixed in the desired position.

Figure 5:
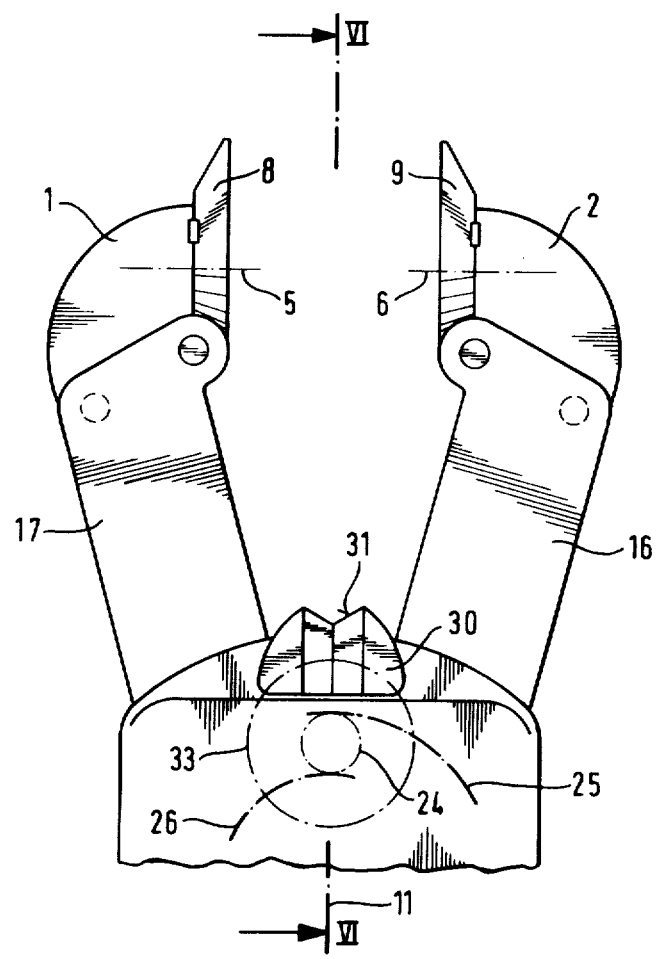

In the free space between the clamping plates 1, 2 or respectively the hinge quadrangles 3, 4 supporting them there is removably disposed a bridge 30 in the embodiment shown in FIGS. 5 and 6 above the drive parts 24,25, 26. The bridge protects these drive parts and the side housing parts against excessive force and damage and is provided at its upper side with prismatic or groove-like guide surfaces 31 for depositing clamped, and in particular elongated articles such as the hammer indicated in FIG. 6 in dot-dash lines. Important is here again the exchangeability of this bridge 30, which allows various resting prism, additional tensioning surfaces or special functions with tool like character such as cutting and the like, to be used.

In order to allow for releasing of a clamped in object, which is fixed by a gripping force or by a locking mechanism, even in case the drive system is interrupted or is defective, then advantageously a safety coupling not shown can be coordinated with the drive for the hinge quadrangles 3,4, which for example can be actuated by a lever from the outside, whereby the two clamping jaws 1,2 are decoupled from the drive system and thereby become freely rotatable around the axis 10.

The control of the tilting motion around the axis 10 can be provided either actively by way of a motor and a self-blocking drive or by hand, wherein in the latter case a fixation in catch position or stepless by frictional coupling can be provided.

I claim:

1. An artificial hand comprising:
   a support rotatable about a first axis;
   a ring mounted on said support for rotation about a second axis constituting the axis of said ring and perpendicular to said first axis;
   a pair of hinge quadrangles each having a first limb pivotally connecting the said ring for rotation therewith, a second limb generally parallel to said first limb and having an end displaceable along said ring whereby extensions of said second limbs intersect at said second axis whereby said quadrangles virtually have a common pivot axis coinciding with said second axis, and a third limb articulated to said first and second limbs;
   respective clamping jaws pivotally mounted on the respective hinge quadrangles and tiltable relative thereto about a respective third axis generally transverse to a plane common to said first and second axes, said jaws being juxtaposed for engagement of objects therebetween and being displaced toward and away from one another by swinging movement of said second limbs toward and away from one another; and
   means for angularly displacing at least one of said jaws about the respective third axis relative to the respective hinge quadrangle and for relatively displacing said second limbs of said hinge quadrangles.

2. The artificial hand defined in claim 1 wherein each of said second limbs is guided on said ring by a circular bearing disposed coaxially with said ring.

3. The artificial hand defined in claim 2 wherein said means for relatively displacing said limbs of said hinge quadrangles includes a pinion and respective gear segments connected to said second limbs and meshing with said pinion.

4. The artificial hand defined in claim 2 further comprising drive means including a motor, a gear driven by said motor and a further gear rotatable about said second axis and meshing with the motor driven gear for rotating said ring on said support about said second axis.

5. The artificial hand defined in claim 2, further comprising a hand wheel rotatable about said second axis and connected with said ring for tilting same about said second axis.

6. An artificial hand defined in claim 2 wherein said jaws are formed along confronting surfaces with grooves engageable with said object whereby said object can entrain the other of said jaws with said one of said jaws.

7. The artificial hand defined in claim 2, further comprising a replaceable bridge disposed between the hinge quadrangles and formed with guide surfaces for stabilizing an object held in said jaws.

8. The artificial hand defined in claim 2 wherein said clamping jaws are formed as gripper plates replaceably mounted on the respective hinge quadrangles.

* * * * *